United States Patent [19]

Maloney et al.

[11] 4,386,911
[45] Jun. 7, 1983

[54] PRESSURIZED IRRIGATING ORAL SCRUBBER

[76] Inventors: Holly H. Maloney; Albert L. Maloney, both of 16 Rue Grand Vallee, Newport Beach, Calif. 92660

[21] Appl. No.: 325,635

[22] Filed: Nov. 30, 1981

Related U.S. Application Data

[63] Continuation-in-part of Ser. No. 152,341, May 22, 1980, abandoned.

[51] Int. Cl.³ ............................................. A61C 3/06
[52] U.S. Cl. .................... 433/125; 433/166; 433/82
[58] Field of Search ................. 433/89, 80, 82, 166, 433/125

[56] References Cited

U.S. PATENT DOCUMENTS

2,017,881 10/1935 Wiseman ............................. 433/166
3,939,599 2/1976 Henry et al. ......................... 433/125
4,259,071 3/1981 Warden et al. ...................... 433/166

FOREIGN PATENT DOCUMENTS

197803 3/1978 France ................................ 433/125

Primary Examiner—Robert Peshock
Attorney, Agent, or Firm—George F. Bethel; Patience K. Bethel

[57] ABSTRACT

The following disclosure discloses a pressurized irrigating oral scrubber for the removal of bacterial plaque and deleterious residue and food particles on a user's teeth. The irrigator incorporates a pressurized source of fluid, such as a liquid in the form of tap water or a solution of water and oral hygienic material. The source of fluid can be provided by fluid under pressure that has been reduced, such as from a tap, or a pumping unit which pressurizes the fluid for irrigation purposes. The fluid which is pressurized is delivered through a nozzle or opening to the areas to be irrigated in adjacent relationship to a concave scrubbing cup. The scrubbing cup has a concave or depressed area therein with a relieved surface within the cup in the form of ribs or protuberances to allow for a scrubbing function of the teeth in the area between the gums and the teeth as well as the teeth, while at the same time irrigating and rinsing the residue as it is scrubbed and removed by the scrubbing cup. A series of vents or slits in the peripheral edge of the scrubbing cup allows the cup, which is made of a soft, flexible material, to open slightly like flower petals against the tooth surfaces. This condition permits the flattening of the cup surface against the teeth to aid in scrubbing and also to allow pressure release of fluid passing through the cup.

21 Claims, 20 Drawing Figures

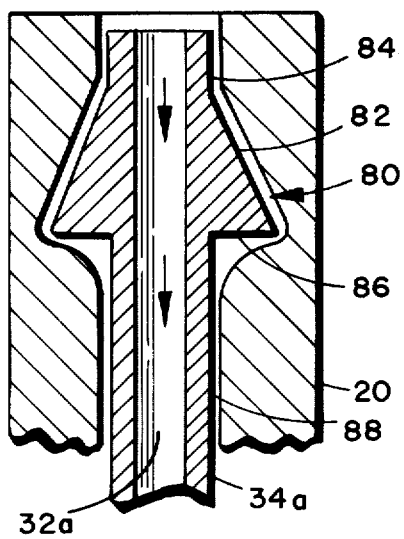
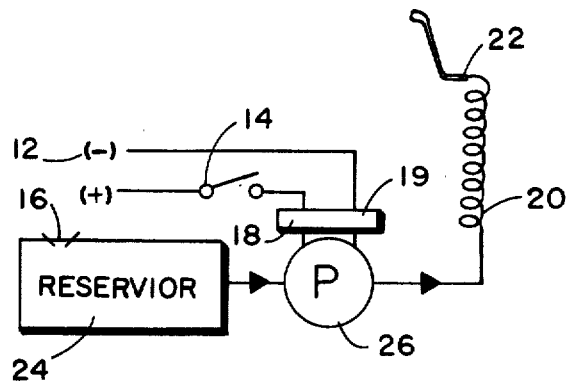
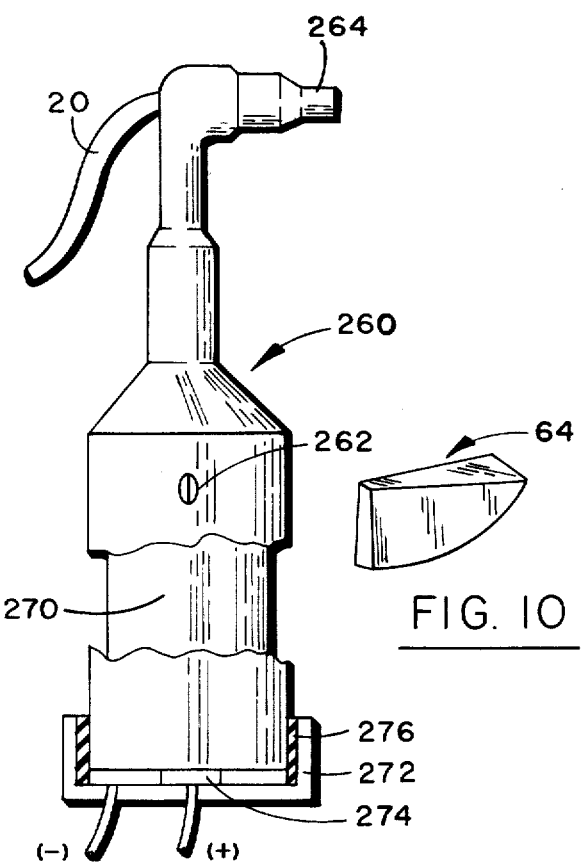
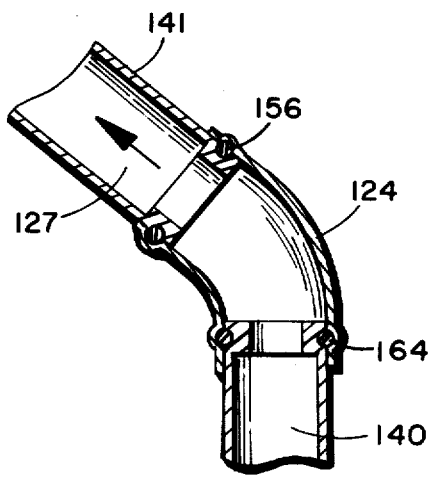
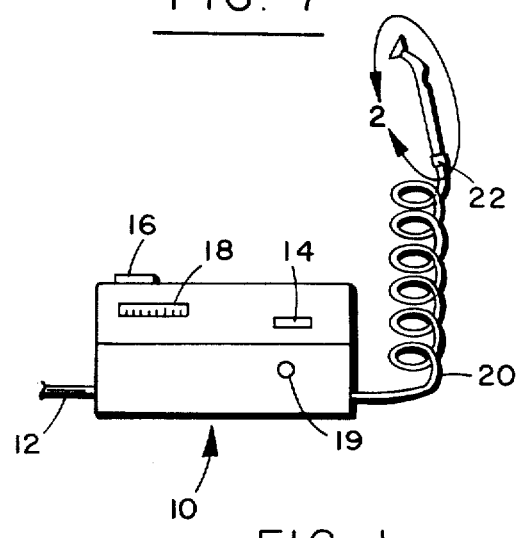

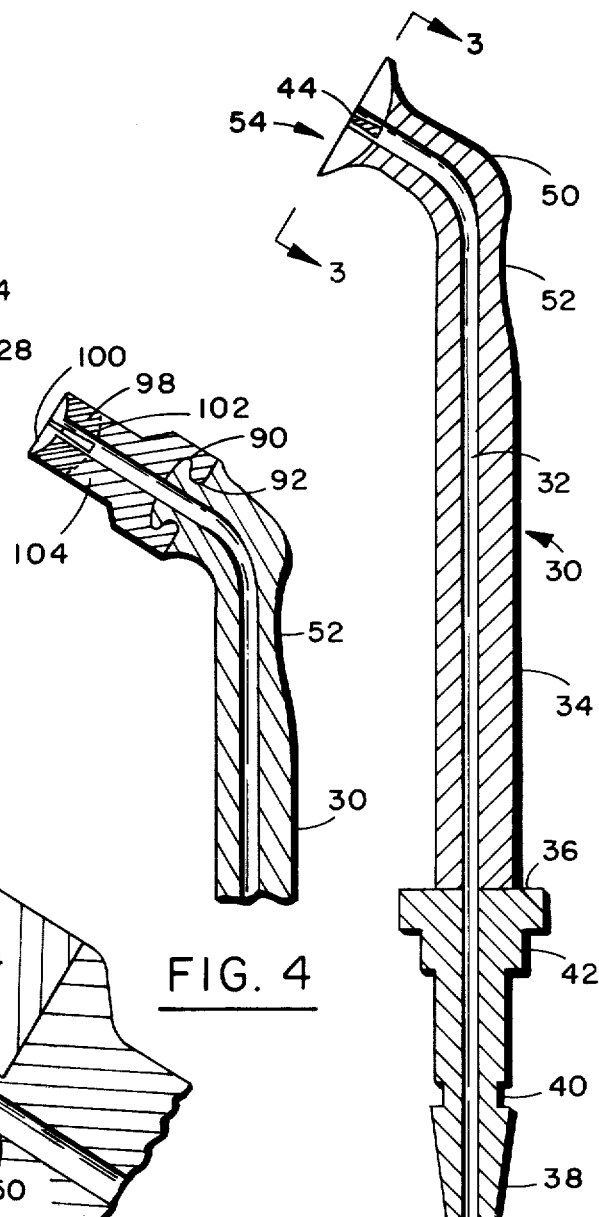

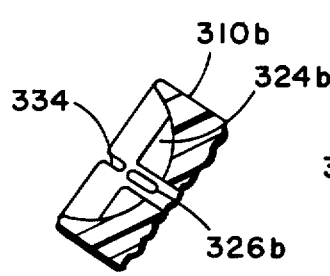
FIG. 17
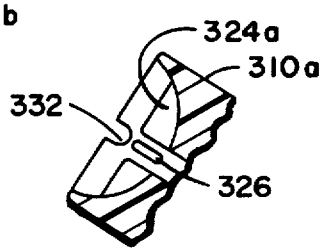
FIG. 16
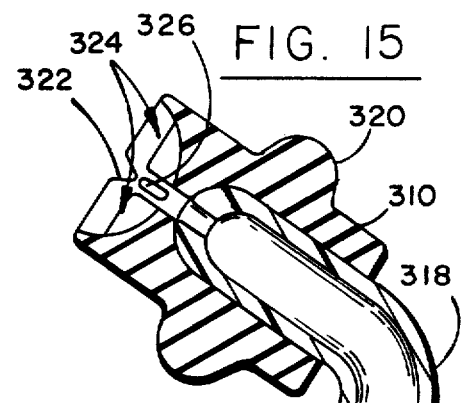
FIG. 15
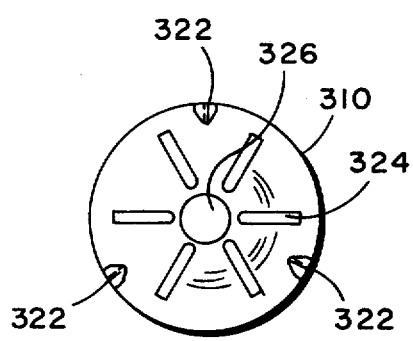
FIG. 18
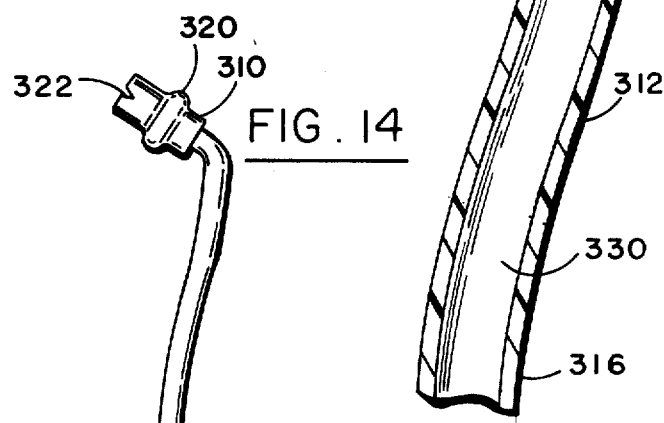
FIG. 14
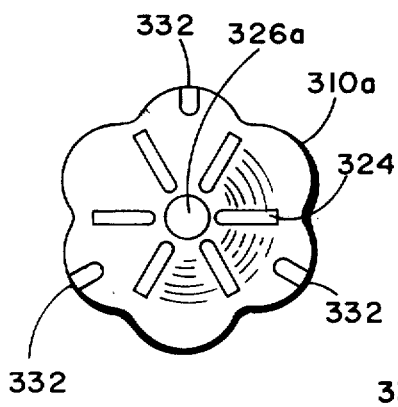
FIG. 19
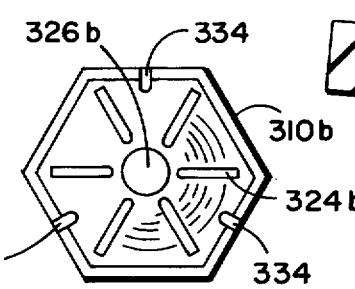
FIG. 20
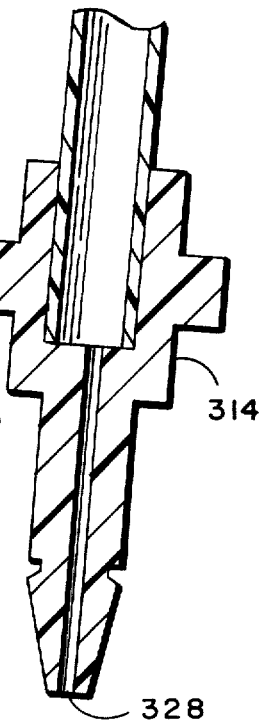

PRESSURIZED IRRIGATING ORAL SCRUBBER

This case is a continuation in part of our previously filed case for a pressurized irrigating oral scrubber, bearing Ser. No. 152,341 and filed on May 22, 1980 now abandoned.

BACKGROUND OF THE INVENTION

1. Field of the Invention

The field of this invention lies within the oral hygiene art. In particular, it lies within the art of providing a pressurized source of fluid, such as water, to a user's mouth for purposes of irrigated removal of bacterial plaque and other deleterious residue and food particles.

2. The Prior Art

The prior art related to the scrubbing and irrigated removal of bacterial plaque and residue incorporates various professional dental equipment and home remedies. The professional dental equipment incorporates individual irrigation means in the form of sprays under pressure from various nozzles and configurations that are used in adjacent relationship to a dental chair. In addition thereto, various means for scrubbing residue and bacterial plaque from a user's teeth have been incorporated with rotary driven devices by means of linkages and belts that are well known in the art.

In addition to the foregoing dental usages, there are various means for irrigating teeth by certain home remedies. In particular, one has been particularly popular which incorporates a pulsating flow of fluid out of a nozzle that can be placed in adjacent relationship to the gums. The pulsating source of fluid is sold under various trademarks and has been broadly utilized. The flow of fluid usually is directed toward the interface between the gums and the teeth, or the area between each respective tooth in order to provide a flushing or irrigation of any residue, bacterial plaque or food particles therein.

The drawback of the foregoing device is that it does not sufficiently abrade or remove the material on the surface of the teeth. This is due to the inability to provide sufficient fluid pressure for flushing or hydraulically removing the food particles and in particular, bacterial plaque and residue. If the hydraulic pressure were sufficient to remove the bacterial plaque and residue on the surface of the teeth, it would possibly damage the gums and the teeth, as well as portions of the oral cavity. The foregoing is particularly true when the hydraulic pressure engages the gum line or the area between the teeth. Such gear surges and hydraulic pressures tend to disengage the gums from the interface of the teeth if used with sufficient pressure to dislodge a substantial amount of coating material from the teeth. Furthermore, inasmuch as bacterial plaque is substantially lodged and adhered to the surface of the teeth, it becomes difficult to remove it by hydraulic pressure.

As a consequence of the foregoing, the only practical way today of removing bacterial plaque, residue and certain coatings from the teeth is by means of scrubbing with a brush or through the utilization of dental floss and certain picks and interfacial tooth cleaners. Aside from the foregoing, there is no practical way of removing the residue and bacterial plaque. Furthermore, there is no way of removing the foregoing with an irrigating process in concert therewith.

This invention overcomes the deficiencies of the prior art by allowing a simultaneous irrigation and scrubbing process for the removal of bacterial plaque, residue and food particles, without damaging the gumline or teeth. This is accomplished by an irrigation of sufficient pressure to flush the bacterial plaque and residue from the teeth that has been removed through the scrubber that is utilized with the irrigator.

The scrubber incorporates a channel through which irrigating fluid can be provided. At the same time, the scrubber incorporates a number of scrubbing surfaces that have been relieved from a general concavity or a depression within the scrubber. The scrubber is in the form of a scrubbing cup or other concave or depressed member having a peripheral wall which can serve a portion of the scrubbing function, while at the same time having a number of ribs or protuberances which provide a relieved surface for scrubbing.

The scrubber is of sufficient flexibility and resiliency to be slightly flattened during its scrubbing mode so as to open up the depressed area for the exposure of the relieved surface to a greater degree. In this manner, the relieved surface or ribs of a scrubbing cup can be rubbed across the surface of the teeth and the gumline, for removal of bacterial plaque, residue and food particles. During the removal process, an irrigation and flushing thereof takes place or the irrigation and flushing can be turned on at a later point in time for irrigated removal of the scrubbed residue and bacterial plaque.

During normal use of the scrubber, there is a buildup of fluid pressure between the scrubbing cup and the tooth surface. This pressure is then released all at once in the area of the sub-gingival area of the gums. This condition is undesirable since it has been shown to predispose the gingival area to low grade infection. According to a particular feature of the invention the peripheral wall of the scrubbing cup is provided with a series of vents in the form of notches, slits and the like. Upon contact of the scrubber with the tooth surface, the wall of the scrubber fans outwardly like separate flower petals. This permits the fluid pressure to be released gradually through the vents, while at the same time aiding the scrubbing away of plaque and other debris and the subsequent rinsing away thereof.

The foregoing device creates a combination which has been unknown to the prior art and which is particularly beneficial in the maintenance of good dental health and hygiene. As a consequence, it is a substantial step over the prior art and should be read broadly in light of the following specification in consideration of the claims that follow hereinafter.

SUMMARY OF THE INVENTION

In summation, this invention comprises a combination scrubbing device in the form of a depressed relieved resilient member or cup having an irrigating means that provides hydraulic pressure in conjunction with the scrubbing provided by the scrubbing member.

More particularly, the invention utilizes a source of hydraulic pressure, such as water, from the tap or a pump. The pressurized fluid in the form of water can be provided with a hygienic material to provide a dental hygiene solution to cleanse as well as freshen the mouth.

The source of fluid pressure can be provided by means of an electrically driven pump that operates on a constant pressure or pulsating pressure basis. The constant or pulsating pressure can be such that it can be raised or lowered, depending upon the degree of hydraulic pressure required for irrigation of the gums and teeth, without deleterious effect on the gums.

The fluid which is delivered is provided through a scrubbing member having a passage therethrough in fluid connected relationship to the fluid under pressure. The scrubbing member has a plurality of protuberances or ribs that provide a relieved surface. The relieved surface can be provided in any particular manner, so long as it creates a situation wherein an abrading or scrubbing effect is provided.

The outer periphery of the scrubbing cup can be of any particular peripheral configuration with a depression or downwardly sloping walls interiorly thereof, leading to the opening for the introduction of fluid under pressure. Furthermore, the relieved surface can be in the form of ribs, striations, bumps, notches, or other means to create a relieved surface that can be utilized in scrubbing one's teeth.

The material out of which the scrubbing member is made can be of a silicon or elastomeric resilient material to flex sufficiently while at the same time deforming only to the extent necessary to protect the gums of a user and maintain the abrading or relieved surface in contact with the teeth and the gums.

DESCRIPTION OF THE DRAWINGS

The invention will be more clearly understood by reference to the description below taken in conjunction with the accompanying drawings wherein:

FIG. 1 shows a side elevation general view of the apparatus of this invention that can be a preferred embodiment thereof;

FIG. 2 shows a midline sectional view of the irrigator and scrubbing member enriched by circle 9 of FIG. 1;

FIG. 3 shows a frontal view of the scrubbing member of this invention as seen in the direction of lines 3—3 of FIG. 2;

FIG. 4 shows an alternative embodiment of the invention showing a removable scrubbing device thereof;

FIG. 5 shows a detailed view of a scrubbing device as threaded to its base conduit;

FIG. 6 shows an alternative embodiment of the device within a rotational scrubbing member;

FIG. 7 shows a detail of the sleeve to provide fluid to the rotational scrubbing device of FIG. 6;

FIG 8 shows a schematic view of a reservoir, pump and oral scrubbing device of this invention that can be derived from the general showing of FIG. 1;

FIG. 9 shows a detailed view of a coupling for the scrubbing device of this invention attached to the tube for the delivery of fluid therethrough;

FIG. 10 shows a detail of one of the ribs of the scrubbing device;

FIG. 11 shows an alternative scrubbing device of a triangular rather than a rounded configuration;

FIG. 12 shows a second alternative scrubbing device having a hexagonal outer periphery with small bumps or protuberances for relieved scrubbing members;

FIG. 13 shows a fragmented view of an alternative embodiment of this invention utilizing a battery powered rotatable cup;

FIG. 14 shows a side elevation of the vented scrubbing device of the invention;

FIG. 15 shows a midline sectional view of the vented scrubbing device of FIG. 14;

FIGS. 16 and 17 show detailed midline sectional views of vented scrubbing devices having U-shaped vents and slit vents respectively; and, FIGS. 18, 19 and 20 show alternate scrubbing cup configurations with V-shaped vents, U-shaped vents and slit vents respectively.

THE PREFERRED EMBODIMENTS

Looking more particularly at FIG. 1, it can be seen that a unit 10 has been shown. The unit 10 has been connected to a power source by a cord 12 and has a switch 14 for providing an on and off control of the unit. In addition thereto, a reservoir opening 16 is provided. A pressure switch 18 adjustment is shown which is a thumb wheel adjustable pressure switch. The pressure switch 18 allows for variable control of the amount of pressure that is delivered by the unit. Also, the unit is provided with switch means 19 to shift between a pulsating flow to a constant flow of fluid.

The unit 10 has a tubular extension or hose 20 extending therefrom that terminates at a coupling 22. Schematically, the foregoing unit 10 is shown in FIG. 8, wherein a reservoir 24 of fluid is provided in connected relationship to a pump 26. The pump 26 is operated by the switch 14 which is shown in schematic form across a power source provided by line 12.

The tube 20 which is connected to the coupling 22 can be detached from the pump and cleaned. In addition thereto, the tube 20 can be provided with a coupling for connecting it to a source of tap water so that fluid pressure can be provided from common residential water pressure.

The reservoir 24 can be filled with fluid that is provided with a solution of hygienic material. The solution can be of any known solution for providing good hygiene and freshening of the mouth.

The entire intent of the foregoing device is to deliver sufficient fluid pressure with regard to a liquid that is either provided with an orally hygienic solution or plain water through a pulsating or constant flow manner.

Looking more particularly at the showing of FIG. 2, which is the detailed showing of the device connected to coupling 22, it can be seen that a bent tubular member 30 is shown with a conduit 32 passing therethrough. The bent tubular member 30 has an upright shaft 34 which is connected to a flange 36 that in turn incorporates a slanted insertion member 38 with an undercut 40 and ridge 42. The foregoing elements 36 through 42 comprise the coupling 22 to effectuate a fluid tight connection between the line 20 and the shaft 34. This allows for fluid to flow from the line 20 through the conduit 32 toward an opening 44 of the tubular conduit 32. Other types of couplings can be utilized to connect the device to a hose, such as that shown in FIG. 9 that is described hereinafter.

The tubular conduit 32 has been shown as a conduit passing through the midsection of a shaft 34 that can be made of any particular material such as plastic, metal or other kinds of material. Furthermore, as can be seen, a bend 50 has been shown with a depression 52. The bend 50 allows for the scrubbing cup 54 to be exposed to the teeth of a user at a handy angle. However, the bend 50 is not necessary and furthermore, other configurations suitable for various oral orientations can be utilized.

The depression 52 is for receipt of a finger for holding the shaft 30. However, it should be understood that the depression 52 is also not necessary and other finger holding means or finger articulation means can be utilized with the instant device, so as to allow for various manual articulations of the entire shaft 30.

The scrubbing cup or member 54 can be seen in greater detail in FIG. 3 wherein an outer peripheral wall 60 comprising a plurality of arcuate members terminating in slight depressions 62 surround and provide the periphery of the scrubbing member.

A plurality of ribs 64, one of which has been shown in detail in FIG. 10 are formed and molded within the cup and terminate at ends 66, thereby providing an upstanding wall. The ribs 64 can be substituted by any other particular relieved surface, such as striations, undulations, bumps, and other protuberances. The round periphery of the scrubbing cup provided by the arcuate members 60 can also be completely rounded, oblong, ogive, or in any other suitable configuration. This is true even to the extent of the showing of FIGS. 11 and 12 wherein triangular and hexagonal members are shown. The members of FIGS. 11 and 12 have side walls 70, 72, 74 and 77 through 87. Additionally, a plurality of protuberances 76 and 76a in the manner of little bumps, are shown respectively within the inner portions of the triangular and hexagonal members.

In addition to the foregoing configurations, rectangular or other shapes can be utilized with various protuberances, bumps or relieved surfaces in an interior depression, including octagonal and pentagonal peripheries. The general requirement is to have a relieved surface with an outer peripheral wall and depressions within the peripheral wall to provide for limited resilient flexible movement of the outer walls and inner walls, such as wall 64. To this end, the material of the scrubbing cup 54 should be made of a resilient elastomeric or plastic material, such as silicon, rubber, or other suitable plastic or elastomeric material that will allow for resilient flexibility. The material should be sufficiently flexible so as to avoid damage to the gums, while at the same time sufficiently resilient to provide the scrubbing necessary for the removal of bacterial plaque, residue and food particles.

The above configuration or coupling of FIG. 2 can be substituted by a coupling shown in FIG. 9 between the tube 20 and the shaft 30 which has been shown as shaft 34a in FIG. 9. In this embodiment, a flared arrow shaped member 80 has been shown with a sloped sidewall 82 terminating in an upper portion 84 with a substantial flange 86 at the base thereof. The tubular portion 88 receives fluid in the direction of the arrows 90 to effectuate the flow of fluid upwardly through the walls of the tube 20. This coupling could be utilized with elastomeric sidewalls of a tube 20 having sufficient resiliency so that the tube can be pulled in and out to provide multiple types of scrubbing cups attached to the shaft 34a with the passage 32a therethrough.

The foregoing coupling configurations allow for a delivery of fluid through the center opening 63 of the member or cup shown in FIG. 3, or the opening 73 or 75 in the members shown in FIGS. 11 and 12. The fluid flow through conduit 32 is of course under pressure and either pulses out of the openings 63, 73 or 75, or can be delivered in a steady stream at any variable pressure as provided by the variable pressure adjustment of thumb wheel 18.

In order to provide for interchangeable scrubbing members on the same shaft 30, a coupling has been shown in FIG. 4 wherein an enlarged mushroom head 90 of FIG. 4 has an undercut 92. The undercut receives a circumferential gripping flange 94 in the form of a round circular interior flange that seats within the undercut 92 of the mushroom 90. In this showing there are also a number of ribs 98 and 100 that are shown in cross section and side view respectively inasmuch as there is a midline section. In this embodiment the scrubbing cup of FIG. 4 has four ribs that are relatively upstanding in their configuration and terminate at a base surface 102 of base 104. The material of which the scrubbing member is made can also be an elastomeric or resilient plastic material such as silicon rubber providing sufficient resiliency to the ribs 98 and 100, or protuberances therein, while at the same time having sufficient flexibility so as to not damage the gums or teeth of a user.

As an alternative to the foregoing, a rotational scrubbing cup 110 has been shown having interior ribs 112 and 114 with a passage 116 therethrough analogous to outer passage 44 and passages 63, 73 and 75. The scrubbing cup 110 is attached by means of the mushroom configuration analogous to FIGS. 4 and 5. However, in this case, the mushroom member 90 is attached to a gear 120 which has a passage 121 passing therethrough with a flexible coupling 124 that provides for connection to a second passage 126 passing through a gear 128. The detail of the coupling is shown in FIG. 7 wherein a sleeve having internal bearing surfaces is shown. The sleeve with the internal bearing surfaces allows for the gears 120 and 128 to turn with the provision of fluid in the direction of arrow 127 delivered from conduit 121 as originated from conduit 126.

The gears 120 and 128 allow a turning of the scrubbing cup 110 by means of a drive provided by the outer walls of the conduit 126. In other words, shaft 140 is shown turning the gear 128 in a manner whereby the gear will turn the second gear 120 to turn the scrubbing cup 110 and provide for an irrigating fluid therethrough. The coupling shown in FIG. 7 can be such that the sleeve 124 has internal ring seals 156 at the upper end connected to shaft 141 and a lower ring bearing 164 that engages a groove within shaft 140 in the same manner as ring bearing 156 engages a groove in the sleeve 124.

The entire configuration allows for the delivery of fluid through the shaft 140 and 141 while at the same time allowing an angular turning at the angle by means of the gears 120 and 128 so that the scrubbing cup 120 turns to provide for rotational movement thereof. This, of course, allows for protuberances or ribs such as ribs 112 and 114 to abrade and turn against the teeth.

Looking more particularly at FIG. 5, it can be seen that a different form of scrubbing cup has been shown. The scrubbing cup incorporates a base member 52 or conduit similar to the one shown in the prior configurations. The conduit has a set of threads 250 extending therefrom which can either be formed of the same material or inserted in the form of a shank into the material forming conduit 52. The threads can also be metallized in the form of a shank that has threads extending therefrom. A cup or head 252 is shown having threads 254 with matching threads 250 for allowing the cup to be threaded over the threads 250. In this manner, an accommodation of the cup 252 can be made whereby it is threaded to the threads 250 so that any flow of fluid can be provided therethrough in the manner shown in the previous configurations such as FIG. 4 with the mushroom attachment. The threads can be reversed as to their male and female orientation.

In all other matters, including the tip of the cup, the configuration is the same and has been numbered accordingly.

Looking more particularly at FIG. 13, it can be seen that a battery powered scrubbing device 260 is shown. The battery powered scrubbing device is attached to a conduit 20 for purposes of providing fluid thereto. This fluid can be under pressure, such as the pump pressure provided by pump 26, or fluid pressure can be deliverable through the conduit 20 by means of an attachment to a tap. The instant device incorporates a battery switch 262 that allows a motor therein to turn the head or cup 264. The cup 264 is attached to a turning head 265 in the same manner as the cup shown in FIGS. 4 and 5 or by any other suitable means. The gear train for driving the cup 264 is similar and analogous to that shown in FIG. 6. However, in this instance, the gears are at a ninety degree angle rather than at the angle shown therein. Furthermore, the conduit 121 is directly connected with direct throughput to the tube 20 to allow delivery from the cup 264.

The foregoing device is battery powered by batteries 270 which can be recharged in a base 272 that is well known in the art. The base 272 is connected to a positive and negative power source that can charge the batteries through a positive contact member 274 and negative contact member 276 in the base 272.

The entire device enables one to turn the switch 262 after removal from the base 272 and cause the cup 264 to rotate. In this manner, fluid can be delivered through the conduit 20 through the cup 264 in like manner as that shown in FIG. 6 where a rotatable cup 110 is shown attached to the drive gears therein.

The foregoing allows for a portable battery operated unit which can be easily utilized and charged without the necessity of having electrical current in adjacent relationship to a fluid delivery means through the conduit 20. This makes for a safer and more portable unit.

Referring to FIG. 15, there is shown a midline sectional view of an alternate embodiment of the irrigator and scrubbing device of the invention. As shown, the scrubbing cup 310 is in connected relationship to a somewhat rigid bent tubular member 312 which is connected to a coupling 314, similar to that shown in FIG. 2. A depression 316 in tubular member 312 provides a convenient finger hold for grasping the device during use, and permits the tubular member 312 to act in a springlike manner. This provides better control of the pressure of the scrubbing cup against the teeth. In order to expose the scrubbing cup 310 to a convenient angle to the teeth during use, the tubular member 312 is also bent at point 318 near its end to an angle which provides optimum presentation of the face of the scrubbing cup 310 to the teeth during use.

The combination of the finger bend or depression 316 and the bend 318 at the end of the tubular member 312, greatly enhances control of the scrubbing cup during use, as well as improving the effectiveness thereof. Thus, when the tubular member 312 is held upright with the scrubbing cup 310 facing the teeth, the pressure of the scrubbing cup against the teeth is controlled by hand and finger pressure. The angle of presentation of the scrubbing cup 310 enables the cup to be easily placed on the tooth surfaces, in crevices between teeth, under the gumline and the like for optimum scrubbing of the tooth surfaces. The depression or bend 318 enables the scrubbing cup 310 and tubular member 312 to act as an extension of the user's finger. Consequently, even normally hard to reach areas of the mouth are easily scrubbed.

The tubular member 312 can be constructed of any material, such as plastic, metal, or other types of materials. Similarly, the coupling 314 can also be made of plastic, metal, or other materials.

As shown in FIG. 15, the scrubbing cup 310 is slip fit over the end of the tubular member 312. Circumferentially around the center of the length of the scrubbing cup 310 is a reinforcing rib or flange 320.

The major difference between the design of the scrubbing cup 310 and the previously described scrubbing cups of FIGS. 1 through 13, is the provision of one or more vents along the peripheral edge of the scrubbing cup 310. For example, in scrubbing cup 310, the vent shown 322 has a V-shaped configuration. In other respects the scrubbing cup is similar to those shown in FIGS. 1 through 13, including internally oriented ribs, protuberances, bumps, or relieved surfaces in the central depression thereof. For example, the scrubbing cup shown in FIG. 15 includes ribs 324 which surround the central opening 326 through which the fluid is ejected. Thus, during operation fluid enters the opening 328 of coupling 314 and progresses through the interior 330 of tubular member 312 and out through the opening 326 of scrubbing cup 310.

Looking more particularly at the remaining figures, there are shown other types of vents used in lieu of the V-shaped vent 322 of scrubbing cup 310. For example, in the scrubbing cup 310a of FIG. 16, the vent 332 has a U-shape, and in FIG. 17 there is shown a slit vent 334 in the periphery of scrubbing cup 310b.

As illustrated in FIGS. 18, 19 and 20, the vents having various configurations can be inserted in scrubbing cups of various configurations. As shown in FIG. 18, the periphery of the scrubbing cup 310 has a V-shaped vent 322 while in FIG. 19 there is a U-shaped vent 332 disposed in the periphery of a scalloped configuration of a scrubbing cup 310a. In FIG. 20 there are slit vents 334 disposed in the periphery of a hexagonal configuration of a scrubbing cup 310b. The scrubbing cups shown in FIGS. 18, 19 and 20 have central scrubbing ribs 324, 324a and 324b respectively.

The exact vent configuration in the periphery of the scrubbing cup is not critical. The drawing shows V-shaped, U-shaped, and slit vent configurations. Other vent configurations such as round, oval, and the like can also be used and are considered to be a part of this invention.

While the scrubbing cups shown in the drawings have been shown with three vents, the exact number of vents is not critical. The important thing to achieve is the gradual and continual release of the fluid pressure during use. Therefore, the number of vents should be sufficient to achieve this end. This can be determined empirically as well and is dependent on such factors as the size of the cup, its resiliency, the design of the ribs or other scrubbing protuberances and the fluid pressure of the irrigating device.

Since the scrubbing cups are formed of a soft, flexible material, when the face of the cup is pressed against the surfaces of the teeth, the vents in the peripheral edge of the scrubbing cup allow the division of the edge into separate fanned out portions, similar to petals of a flower. These fanned out areas permit improved scrubbing of the teeth due to the fact that the fanned out areas are flattened along the tooth surfaces and are able to be fitted up under the gumline. At the same time, the scrubbing ribs or protuberances of the central portion of the cup are brought into greater contact with the tooth surfaces. More importantly, the provision of the vents prevents the buildup of fluid pressure against the teeth which might be released suddenly to cause excess pressure to be transmitted to the gum area and consequent damage thereof.

It has been found that the exposure of the sensitive gum tissue to large pressure releases has predisposed the gums to damage and occasionally to a low grade infection. This is thought to occur when plaque is forced into the gums under pressure. By providing the scrubbing cups with vents, the fluid pressure is released over a constant period of time so that there is no buildup of high pressures.

Furthermore, the ability to scrub the teeth and remove plaque and other debris from tooth surfaces, as well as from the gum and crevices between the teeth is improved due to the improved design of this vented scrubbing cup. The inherently resilient and elastomeric nature of the scrubbing cup, allows the cup to spring back to its original configuration upon pulling away from the teeth. At the same time, the vented areas permitting the fanning out as above mentioned also allows for the cup to surround and hold the rounded tooth surfaces. Therefore, the presence of the vent increases the surface contact between the tooth surfaces and the scrubbing cup.

While a user is scrubbing his tooth surfaces with the scrubbing cup using finger pressure to effectively contact the tooth surfaces, the pressurized fluid which is exiting from the central opening within the scrubbing cup removes the food, plaque and other types of materials adhering to the teeth which are desirous of being removed.

It can be readily seen that the above combination provides a more advantageous condition than would be possible with unvented scrubbing cups.

The foregoing configuration shows the utilization of a rotational scrubbing cup with fluid delivered through the center. However, it should be understood that fluid can be delivered in adjacent relationship thereto or through plural openings, or in offset relationship from the axis. In addition thereto, the scrubbing cup member of the remaining figures and the embodiments thereof can be used without the rotational means to provide fluid therethrough of a pulsating or continuous flow to remove bacterial plaque, residue and other food particles in an efficient manner. As a consequence, this invention should be read broadly over the prior art of providing a general scrubbing removal by means of the scrubbing cup or depressed member of this configuration, as well as the irrigated flushing thereof, in the broadest sense, as claimed hereinafter.

We claim:

1. The improvement in a pressurized oral irrigator wherein a source of fluid pressure is provided through a conduit to be delivered to the oral cavity wherein the improvement comprises:
   an outlet from said source of fluid pressure connected to a scrubbing member formed as a scrubbing cup having a depression therein through which the fluid flows, and a relieved surface within said depression, to provide an outer peripheral wall surrounding said cup for scrubbing the surface of the teeth of a user in conjunction with the relief within the depression; and,
   at least one opening through said wall to provide a relief of pressure in said depression and flow through said wall when the cup is blocked at its face.

2. The improvement as claimed in claim 1 wherein:
   said relieved surface comprises a plurality of protuberances on the interior depressed surface of the scrubbing cup wall.

3. The improvement as claimed in claim 1 wherein:
   the outer periphery of said scrubbing cup is rounded.

4. The improvement as claimed in claim 1 wherein:
   the outer periphery of the scrubbing cup is triangularly shaped.

5. The improvement as claimed in claim 1 wherein:
   the outer periphery of said scrubbing cup is hexagonal.

6. The improvement as claimed in claim 1 further comprising:
   an elongated shaft connected to said tube through which the fluid is delivered; and,
   removable connection means between said shaft and said scrubbing cup.

7. The improvement as claimed in claim 1 wherein:
   the outer periphery of the scrubbing member is triangularly shaped.

8. The improvement as claimed in claim 7 wherein:
   said shaft has a a concave curved portion for receipt of a finger thereagainst.

9. The improvement as claimed in claim 1 further comprising:
   an opening passing through said wall formed as a slit in the peripheral surface of said wall.

10. The improvement as claimed in claim 1 further comprising:
    an opening passing through said wall formed as a vent extending from the peripheral surface of said wall.

11. The combination of a source of pressurized fluid and an oral scrubbing member comprising:
    a source of fluid;
    means for causing the fluid to move under hydraulic pressure;
    a conduit connected to said source of fluid;
    a shaft connected to said conduit having a passage for the flow of fluid therethrough; and,
    a concave scrubbing member having a peripheral wall surrounding said concavity attached to said shaft having a relieved surface within the interior periphery of said concavity thereof with a major opening in the face of the concavity through which the pressurized fluid can flow, and at least a second opening in the wall through which fluid pressure can flow when said first opening is blocked across the face.

12. The improvement as claimed in claim 11 wherein said removable connection means comprise:
    a mushroom shaped member with an undercut that receives an interior flange on said scrubbing member; and wherein,
    said shaft has a depression for the receipt of a finger thereagainst.

13. The combination as claimed in claim 11 wherein:
    said second opening is formed as a vent extending from the peripheral surface of said wall.

14. The combination of a source of pressurized fluid and an oral scrubbing member comprising:
    a source of fluid;
    a pump for pumping the fluid under hydraulic pressure;
    power means for said pump;
    a conduit connected to said pump;

a shaft connected to said conduit; and, a scrubbing member having a depression with an opening therein through which the pressurized fluid can flow, the interior walls surrounding said depression having a relieved surface for scrubbing the teeth of a user in conjunction with the periphery of said interior walls, the edge of said periphery having at least one vent therein to release fluid pressure buildup between said member and the surface of the teeth of a user.

15. The combination as claimed in claim 14 wherein:

said source of fluid comprises a reservoir connected to said pump for the provision of fluid;

said scrubbing member has a rounded periphery;

each of said vents is V-shaped;

said relieved surface comprises a plurality of ribs within said depression of said scrubbing member surrounding an opening through which the fluid from said shaft is provided; and, wherein said shaft has a depression along its length for receipt of a finger thereagainst for hand control of the pressure of said scrubbing cup against a user's teeth.

16. The combination as claimed in claim 15 further comprising:

a triangularly shaped scrubbing member having an opening toward the apex thereof; and, a plurality of protuberances within said scrubbing member for providing a scrubbing effect for said scrubbing member.

17. The combination as claimed in claim 14 further comprising:

a removable coupling between said scrubbing member and said shaft for removing said scrubbing member and replacing it on said shaft.

18. The combination as claimed in claim 17 wherein:

said removable connection means comprises a mushroom member attached to said shaft having an undercut thereunder;

a flange on said scrubbing member for receipt in said undercut; and wherein, each of said vents comprises a slit.

19. The improvement in a pressurized oral irrigator wherein a source of fluid pressure is provided through a conduit to be delivered to the oral cavity wherein the improvement comprises:

an outlet from said source of fluid pressure connected to a scrubbing member having a depression area through which the fluid flows from said outlet;

a wall surrounding said depression to provide an outer peripheral member for scrubbing the surface of the teeth of a user in conjunction with the surface within the depression; and, at least one other opening, in addition to said outlet, passing through said wall so that when the surface of said wall is blocked over said depression flow can be maintained from said outlet through said wall.

20. The improvement as claimed in claim 19 wherein said second opening comprises:

a V-shaped vent extending from the periphery of said wall.

21. The improvement as claimed in claim 19 wherein said second opening comprises:

a U-shaped vent extending from the periphery of said wall.

* * * * *